United States Patent
Jachmann (10) Patent No.: US 9,977,118 B2
(45) Date of Patent: May 22, 2018

(54) METHOD OF OPERATING A DISTANCE-MEASURING MONITORING SENSOR AND MONITORING SENSOR

(71) Applicant: SICK AG, Waldkirch/Breisgau (DE)

(72) Inventor: Fabian Jachmann, Freiburg (DE)

(73) Assignee: SICK AG, Waldkirch/Breisgau (DE)

( * ) Notice: Subject to any disclaimer, the term of this patent is extended or adjusted under 35 U.S.C. 154(b) by 0 days. days.

(21) Appl. No.: 15/456,875

(22) Filed: Mar. 13, 2017

(65) Prior Publication Data
US 2017/0261603 A1 Sep. 14, 2017

(30) Foreign Application Priority Data

Mar. 14, 2016 (EP) .................................... 16160167

(51) Int. Cl.
| | | |
|---|---|---|
| G01S 7/48 | (2006.01) | |
| G01S 17/02 | (2006.01) | |
| G01S 17/08 | (2006.01) | |
| G01N 15/02 | (2006.01) | |

(52) U.S. Cl.
CPC ........ G01S 7/4808 (2013.01); G01N 15/0205 (2013.01); G01S 17/026 (2013.01); G01S 17/08 (2013.01)

(58) Field of Classification Search
CPC ...... G01S 7/4808; G01S 17/026; G01S 17/08; G01N 15/0205
See application file for complete search history.

(56) References Cited

U.S. PATENT DOCUMENTS

| | | | | |
|---|---|---|---|---|
| 5,475,494 | A * | 12/1995 | Nishida | G01S 17/936 180/169 |
| 5,504,569 | A * | 4/1996 | Kato | B60T 7/22 180/169 |
| 5,604,580 | A | 2/1997 | Uehara | |
| 9,733,358 | B2 * | 8/2017 | Iwasawa | G01S 17/50 |
| 2008/0244533 | A1 * | 10/2008 | Berg | G06F 11/3447 717/128 |
| 2014/0138518 | A1 | 5/2014 | Hammes | |
| 2015/0077285 | A1 * | 3/2015 | Mahajan | G01C 3/08 342/118 |
| 2015/0276383 | A1 * | 10/2015 | Yoshikawa | G01B 11/14 348/136 |
| 2016/0209499 | A1 * | 7/2016 | Suzuki | G01S 7/4817 |

FOREIGN PATENT DOCUMENTS

| | | |
|---|---|---|
| DE | 19503960 A1 | 8/1995 |
| DE | 10313194 B4 | 7/2006 |
| DE | 102009055990 B4 | 8/2015 |
| EP | 2735887 A1 | 5/2014 |

* cited by examiner

*Primary Examiner* — Sang Nguyen
(74) *Attorney, Agent, or Firm* — Nath, Goldberg & Meyer; Jerald L. Meyer (57) ABSTRACT

The present invention relates to a method of operating a distance-measuring monitoring sensor for monitoring an at least two-dimensional protected field that is divided into a plurality of sector-shaped, cyclically scannable monitored fields, wherein the monitoring sensor comprises at least one light transmitter and at least one light receiver. The invention further relates to a monitoring sensor.

21 Claims, 4 Drawing Sheets

| A | 500 | 1000 | 1500 | 2000 | 2500 | 3000 | 3500 | 4000 | 4500 | 5000 | 5500 |
|---|---|---|---|---|---|---|---|---|---|---|---|
| N | 21 | 11 | 7 | 6 | 5 | 4 | 4 | 3 | 3 | 3 | 2 |

Fig. 4

| Z1 | Z2 | 1 | 2 | 3 | 4 | 5 | 6 | 7 | 8 | 9 | 10 | 11 | 12 |
|---|---|---|---|---|---|---|---|---|---|---|---|---|---|
| 1 | 1 | 5 | 5 | 5 | 10 | 10 | 5 | 5 | 5 | 10 | 10 | 10 | 10 |
| 2 | 2 | 4 | 4 | 4 | 4 | 4 | 10 | 10 | 10 | 10 | 10 | 10 | 10 |
| 3 | 3 | 10 | 10 | 10 | 10 | 5 | 5 | 5 | 10 | 5 | 5 | 5 | 10 |
| 0 | 0 | 10 | 10 | 10 | 10 | 10 | 10 | 10 | 10 | 10 | 10 | 10 | 10 |

Fig. 5

| Z1 | Z2 | 1 | 2 | 3 | 4 | 5 | 6 | 7 | 8 | 9 | 10 | 11 | 12 |
|---|---|---|---|---|---|---|---|---|---|---|---|---|---|
| 1 | 1 | 10 | 1 | 1 | 10 | 10 | 10 | 10 | 10 | 10 | 10 | 10 | 10 |
| 2 | 1 | 10 | 10 | 10 | 10 | 10 | 10 | 10 | 10 | 10 | 2 | 10 | 10 |
| 3 | 2 | 10 | 10 | 10 | 10 | 10 | 10 | 10 | 10 | 10 | 1 | 1 | 10 |
| 4 | 1 | 10 | 10 | 10 | 10 | 4 | 10 | 10 | 10 | 10 | 10 | 10 | 10 |

Fig. 6

| Z1 | Z2 | 1 | 2 | 3 | 4 | 5 | 6 | 7 | 8 | 9 | 10 | 11 | 12 |
|---|---|---|---|---|---|---|---|---|---|---|---|---|---|
| 1 | 1 | 5 | 5 | 5 | 10 | 10 | 10 | 10 | 10 | 10 | 10 | 10 | 10 |
| 2 | 2 | 10 | 10 | 10 | 10 | 10 | 4,5 | 10 | 10 | 10 | 10 | 10 | 10 |
| 3 | 3 | 10 | 10 | 10 | 10 | 4,5 | 10 | 10 | 10 | 10 | 10 | 10 | 10 |
| 4 | 4 | 10 | 10 | 10 | 10 | 10 | 10 | 5 | 5 | 5 | 5 | 10 | 10 |

Fig. 7

METHOD OF OPERATING A DISTANCE-MEASURING MONITORING SENSOR AND MONITORING SENSOR

The present invention relates to a method of operating a distance-measuring monitoring sensor for monitoring an at least two-dimensional protected field that is divided into a plurality of sector-shaped, cyclically scannable monitored fields, wherein the monitoring sensor comprises at least one light transmitter and at least one light receiver.

Such a monitoring sensor can be configured as a laser scanner, for example. A transmitted light beam generated by a light transmitter, e.g. by a laser or the like, is directed via a light deflection unit into the protected field to be monitored and is reflected or remitted there by an object that may be present. The reflected or remitted light moves back to the monitoring sensor again and is detected by the light receiver there. The light deflection unit is designed as pivotable or rotatable as a rule such that the light beam generated by the light transmitter sweeps over a protected field corresponding to the pivot movement or rotational movement. If a reflected light signal received by the light receiver is received from the protected zone, a conclusion can be drawn on the angular location of the object in the protected field from the angular position of the deflection unit.

The distance between the monitoring sensor and the detected object can be determined in a manner known per se on the basis of the time of flight or of the phase shift between the transmitted light and the received light.

If an unpermitted object is located in the protected field, a corresponding object detection signal can be output by the monitoring sensor.

Such monitoring sensors are used, for example, at machines in which, for safety reasons, a danger zone has to be monitored which may not be infringed by an operator during the operation of the machine. If the presence of a non-permitted object, for example a leg of an operator, is detected in the danger zone by the monitoring sensor, a shutdown of the machine or similar is effected on the basis of the object detection signal.

However, small particles such as dust penetrating into the protected field, chips, raindrops or snowflakes that fly around can also result in an unwanted shutdown of the machine. Such false-positive object detection signals reduce the availability of the machine.

It is proposed in DE 103 13 194 B4 that an object detection signal is only generated while taking account of the distance of the object from the sensor and of the angular region over which the object extends when the object has a predefined minimum size.

It is proposed in DE 10 2009 055 990 B4 that only those objects can trigger an object detection signal that are located within the protected field for longer than a predefinable dwell period. This is based on the underlying idea that particles such as chips or the like that may result in an erroneous shutdown of the machine move relatively quickly and therefore leave the protected field again after a brief time.

Since small particles that are located very close to the monitoring sensor can cover a relatively large angular range and can thus mask larger, further remote objects, an object detection signal resulting in the shutdown of the machine also has to be output for safety reasons with particles that fly closely past the monitoring sensor if this were not necessary per se due to the size of the detected particle. This reduces the availability of the machine. An increase in the availability would conversely only be possible at the cost of safety.

It is the object of the invention to provide a method of operating a distance-measuring monitoring sensor that ensures a reliable recognition of objects that satisfy predefined criteria for generating an object detection signal and simultaneously to minimize the frequency of false-positive object detection signals from objects that cannot impair safety due to their size such that the monitoring sensor or a machine monitored by the monitoring sensor can be operated at a high availability.

The object is satisfied by a method having the features of claim 1.

The method in accordance with the invention of operating a distance-measuring monitoring sensor for monitoring an at least two-dimensional protected field that is divided into a plurality of sector-shaped, cyclically scannable monitored fields, wherein the monitoring sensor comprises at least one light transmitter and at least one light receiver, comprises the steps:

transmitting a transmitted light beam into the protected field by the light transmitter;

receiving light that is reflected or remitted by an object that may be present in the protected field by the light receiver;

generating a specific received signal for the respective monitored field on the basis of the received light, wherein a respective received signal comprises information on the angular position of the monitored field and on the distance of an object located therein from the monitoring sensor, wherein all the monitored fields of the protected field are scanned once within a cycle;

determining the size of an angular region over which a respective detected object extends;

determining the size of the object on the basis of the determined distance and on the basis of the determined size of the angular region;

classifying the object as a particle or as a large object on the basis of the determined size of the object and of a predetermined threshold value for the size, wherein the object is classified as a particle if it is smaller than the threshold value and is classified as a large object if it is larger than the threshold value; and generating an object detection signal on the basis of the stored detection signals when it is found that at least one large object is respectively located in at least one of the monitored fields for a predefined first number of sequential cycles or when it is found that at least one particle is located substantially at a stationary angle in at least one monitored field for a predefined second number of sequential cycles.

The cyclic scanning of the monitored fields preferably takes place with the monitoring sensor in accordance with the invention in that pulse-like transmitted light beams are transmitted into the respective monitored fields after one another in time and a specific received signal is generated, and optionally stored, for each monitored field. Discrete angular positions are accordingly scanned.

Since the detection signals are observed over a specific period of time that is determined by the named first number of sequential cycles and by the duration of a respective cycle, not only the size, but also the motion state of an object can be take into account. If an object appears in the same monitored field or fields in each of the sequential cycles, it is considered as an object at a stationary angle. An object at a stationary angle is understood in this context as an object that does not have any movement component or at least no movement component detectable within the framework of the resolution and/or of the measurement accuracy of the monitoring sensor that produces a change of its angular position or a change of the monitored field and therefore in particular also objects dwelling in a stationary, that is unmoving, manner in a monitored field. If, in contrast, an object appears in one or more different monitored fields over the cycles, it must be a moving object. A moving object is in particular understood in this context as an object that has at least one movement component that produces a change of its angular position or a change of the monitored field.

The classification of whether a detected object is a large object or a particle can take place, for example, with the aid of a look-up table for the distance and the angular region or for a value related thereto.

If it was found on the basis of the classification that it is a large object, i.e. an object that at least has the size of a predefined reference object considered critical to safety, an object detection signal is output when it is within the protected field within the named first number of cycles, and indeed independently of its motion state.

In contrast to his, on the detection of a particle not considered critical to safety whose size is smaller than the size of the reference object, an object detection signal is only output when it is found that this object does not move during the predefined number of scanning cycles.

Particles can therefore, for example, be statistically distributed small objects such as chips, snowflakes, raindrops or dust particles that fly around.

In this context, the expression "substantially" at a stationary angle in at least one monitored field means that the particle is not only always located in the same monitored field or fields during the observed period of time, but can also temporarily be present in directly adjacent monitored fields in order nevertheless to satisfy the criterion "at a stationary angle". The circumstance is thus taken into account that, for example, a very small particle that is stationary per se and that is located at the border between two adjacent monitoring fields can be detected in different cycles both in the one monitored field and in the other monitored field due to measuring inaccuracies.

A sector-shaped monitored field is in particular understood as a monitored field that can have both the shape of a segment of a circle or of a sector of a circle and the shape of a spherical segment or of a spherical sector. In a main application, however, a sector-shaped monitored field is a sector-shaped segment for a scanning plane that forms the protected field.

The method in accordance with the invention therefore comprises both test steps, that is, on the one hand, whether a large object is located in at least one of the monitored fields for a predefined first number of sequential cycles and, on the other hand, whether at least one particle is located substantially at a stationary angle in at least one monitored field for a predefined second number of sequential cycles. If at least one of these conditions is satisfied, an object detection signal is generated. Claim 1 is therefore not to be understood such that the method in accordance with the invention were only to comprise two test alternatives.

The term "object detection signal" is to be understood in this respect such that it is generated when the evaluation of the reflected or remitted signals allows an interpretation to the effect that an infringement of the protected field is present.

The named first number of scanning cycles amounts to at least 2, in particular 3, 4 or 5. It is understood that the fixing of this number represents a compromise between the response delay of the monitoring sensor and of the error alarm rate. The number can inter alis also depend on the duration of the scanning cycle to define a sensible observation period.

In this method in accordance with the invention, only particles at a stationary angle (in the above-defined sense) are considered as critical to safety since, when they are close to the sensor, they could possibly mask a large object that is located at a larger distance from the sensor. If, however, particles move within the protected field, even if they are close to the sensor, no object detection signal is generated even though these particles could possibly mask a large object or cast a shadow over it. This is based on the surprisingly simple idea that it is extremely unlikely that a particle and a large object in the shadow of the particle move at the same speed and in the same direction during the observed first number of cycles. Since therefore a distinction is made whether an object identified as a particle on the basis of its size is moved or at a stationary angle, and since an object detection signal is only generated in the latter case, the availability of the monitoring sensor or of a machine connected thereto is increased without safety being impaired.

The first number and the second number of sequential cycles are preferably the same. This simplifies the evaluation required for the generation of the object detection signal. Different numbers and thus different periods of time for which the respective conditions have to be satisfied can, however, also be used as the basis.

In accordance with an advantageous embodiment of the method, an object detection signal is furthermore also generated when it is found for a predefined third number of sequential cycles that at least one large object and at least one particle are each located in at least one of the monitored fields for at least some of these cycles. The case is hereby considered, for example, that a large object is masked or could be masked by a particle at least at times, i.e. for some of the sequential cycles. The safety of the monitoring sensor is hereby increased since the danger of a potential nonrecognition of large objects related to safety is reduced. An availability which may hereby be reduced due to a possibly increased frequency of false alarms can be accepted in this respect.

The first, second and third numbers are preferably the same. Different numbers and thus different periods of time for which the respective conditions have to be satisfied can, however, also be used as the basis here.

In accordance with a further advantageous further development, an object detection signal is furthermore also generated when it is found for a predefined third number of sequential cycles that at least one large object and at least one particle are each located in at least one of the monitored fields for at least some of these cycles and the at least one particle is substantially at a stationary angle. This represents a certain restriction of the previously described embodiment since unlike it the detected particle must be at a stationary angle. As has already been explained above, the underlying idea here is likewise that the likelihood that a large object and a particle masking the large object move at the same speed and in the same direction is extremely small. The availability can hereby be increased without safety being impaired.

In accordance with a further advantageous embodiment, a large object index is provided and a respective particle index is provided for each monitored field, wherein the determination whether at least one large object is located in at least one of the monitored fields for a predefined first number of sequential cycles comprises the large object index being incremented by 1 when the presence of at least one large object was detected in one cycle and the generation of the object detection signal comprises an object detection signal being generated when the large object index has reached the predefined first number, and wherein the determination whether at least one particle is located in at least one monitored field substantially at a stationary angle for a predefined second number of sequential cycles comprises a respective particle index being incremented by 1 in a respective cycle when the presence of a particle in the monitored field associated with this particle index or in a directly adjacent monitored field was detected in a cycle and the generation of the object detection signal comprises the maximum of all particle indices being determined and an object detection signal being generated when the maximum has reached the predefined second number. The named findings and the generation of an object detection signal based thereon can hereby be carried out in a simple manner.

It has proved advantageous in this connection when the generation of an object detection signal comprises, when it is found for a predefined third number of sequential cycles that at least one large object and at least one particle are respectively located in at least one of the monitored fields for at least some of these cycles, the sum of the large object index and the maximum of the particle indices being formed and the object detection signal being generated when the sum has reached the predefined third number. Analog to the above-named embodiment, an object detection signal can be generated in this manner when the case occurs, for example, that a large object is only masked by a particle at times.

Alternatively or additionally, the object detection signals can also be generated on the basis of the sum of the large object index and the maximum of the particle indices for the cases in which only at least one large object or only at least one particle is present in at least one monitored field for a predefined number of cycles.

In accordance with a further advantageous embodiment of the invention, the finding whether at least one large object is located in at least one of the monitored fields for a predefined number of sequential cycles further comprises the large object index being reset when the absence of large objects is detected in a cycle. The finding whether at least one particle is present in at least one monitored field substantially at a stationary angle for a predefined second number of sequential cycles can furthermore comprise a respective particle index being reset in a respective cycle when the presence of a particle was detected for the associated detection field in the directly preceding cycle and the absence of this particle was detected in the current cycle. A resetting of a respective index is in particular understood as a resetting to the value zero. The cases can be taken into account in a simple manner with these embodiments that a large object and/or a particle leaves/leave the protected field before the end of a period of time predefined by the respective number of cycles.

In accordance with an advantageous modification, a resetting of the large object index is omitted when the presence of a particle was detected at the same time within that cycle in which the absence of a large object was detected that was present in the preceding cycle. This e.g. covers the case that a particle suddenly masks a previously already detected large object during an observed number of cycles.

Alternatively or additionally, a resetting of a particle index is omitted when the presence of a large object was detected at the same time within that cycle in which the absence of a particle was detected that was present in the preceding cycle. This e.g. covers the case that a large object suddenly appears during an observed number of cycles that was previously possibly masked by a particle.

The determination of the size of an angular region over which a respective object extends advantageously comprises the size of the angular region being determined on the basis of the number of adjacent monitored fields in which the presence of an object was found at substantially the same distance and their angular intervals being determined. The expression "at substantially the same distance" is in particular also understood as those cases where the received signals for an extended object do not provide identical distance values due to its design or location in space, but where it is very likely that it is a contiguous object and not a plurality of individual objects. Limit values can, for example, be fixed for the respective distance values that allow a finding that the received signals of adjacent monitored fields can be associated with a single object and not, for instance, with two objects that admittedly appear adjacent with respect to their angular positions, but that have different distances from the sensor.

In accordance with a further advantageous embodiment, the received signals generated during a respective cycle are stored for a predetermined number of cycles and the object detection signal is generated on the basis of the stored received signals. The received signals can, for example, be stored in the form of a table, in particular a FIFO (first in, first out) table.

The monitoring sensor is advantageously a laser scanner that is configured for monitoring one or more scanning surfaces. The one or more scanning surfaces can in particular be planar or conical. Accordingly, the protected field can be two-dimensional or three-dimensional in a corresponding manner, wherein with a three-dimensional protected field the laser scanner can have a second scanning direction or can have a plurality of light transmitter/receiver pairs that can e.g. have different azimuth angles.

The invention further relates to a distance-measuring monitoring sensor for monitoring an at least two-dimensional protected field that is divided into a plurality of sector-shaped, cyclically scannable monitored fields, wherein the monitoring sensor comprises at least one light transmitter, at least one light receiver and a control unit, with the control unit being configured for carrying out the method in accordance with any one of the preceding claims.

Further advantageous embodiments of the invention result from the dependent claims, from the description and from the drawings.

The invention will be described in the following by way of example with reference to the drawings. There are shown.

The problem underlying the present invention will first be explained in the following with reference to FIGS. 1 to 3.

Figure 1:
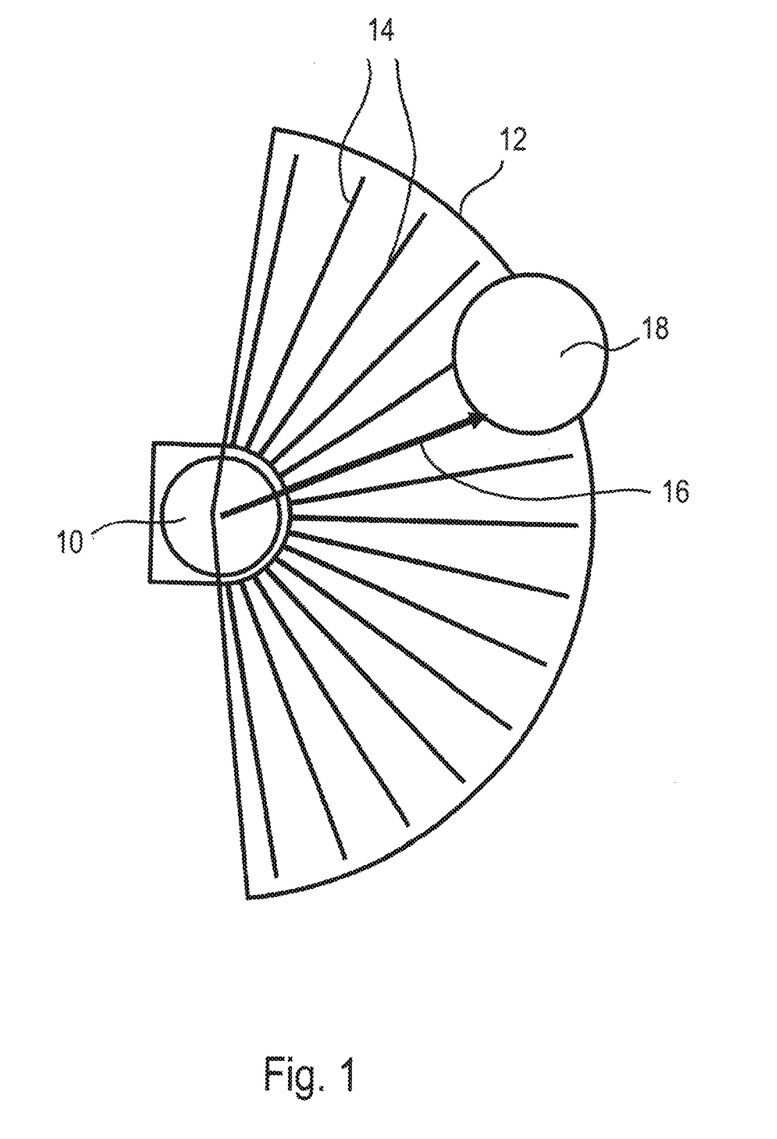
FIGS. 1 to 3 schematic representations of a monitoring sensor for carrying out the method in accordance with the invention in whose protected field objects of different sizes and at difference distances are present.
Figure 2:
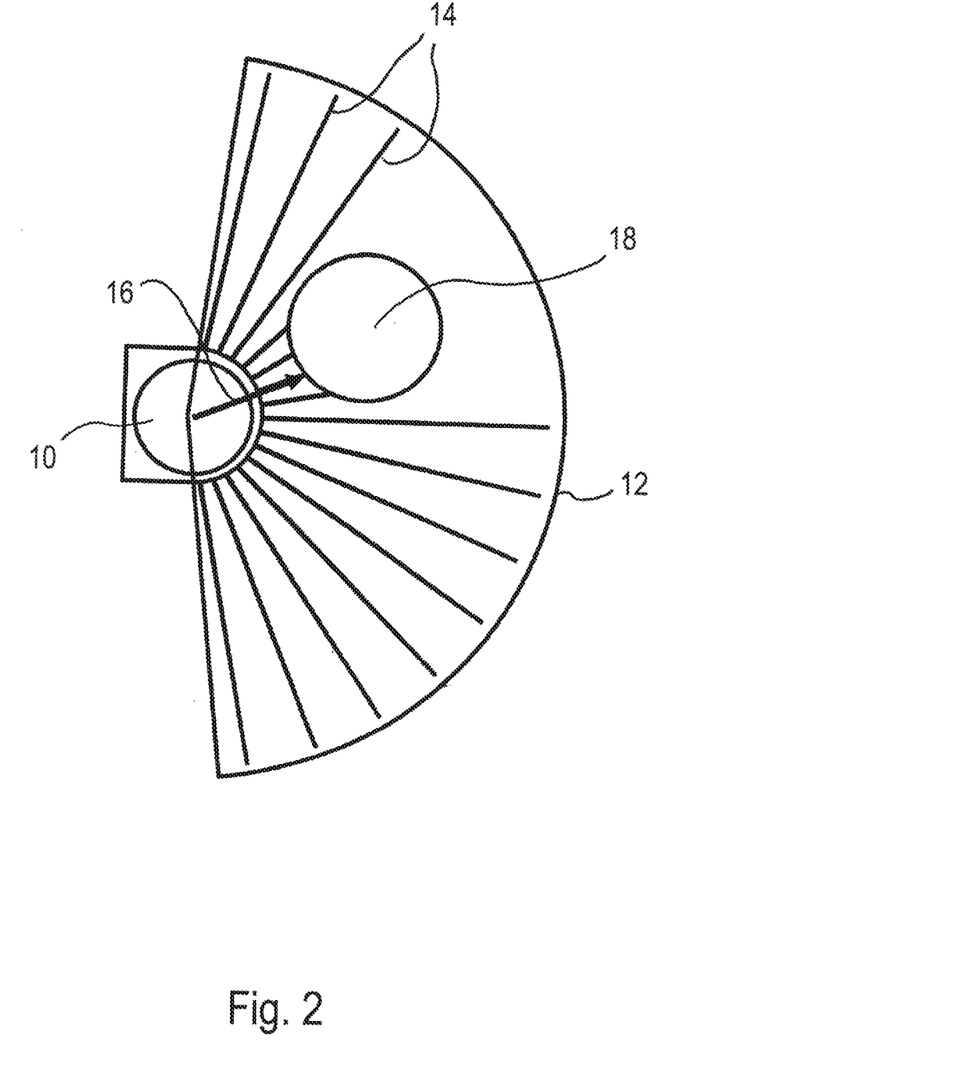
Figure 3:
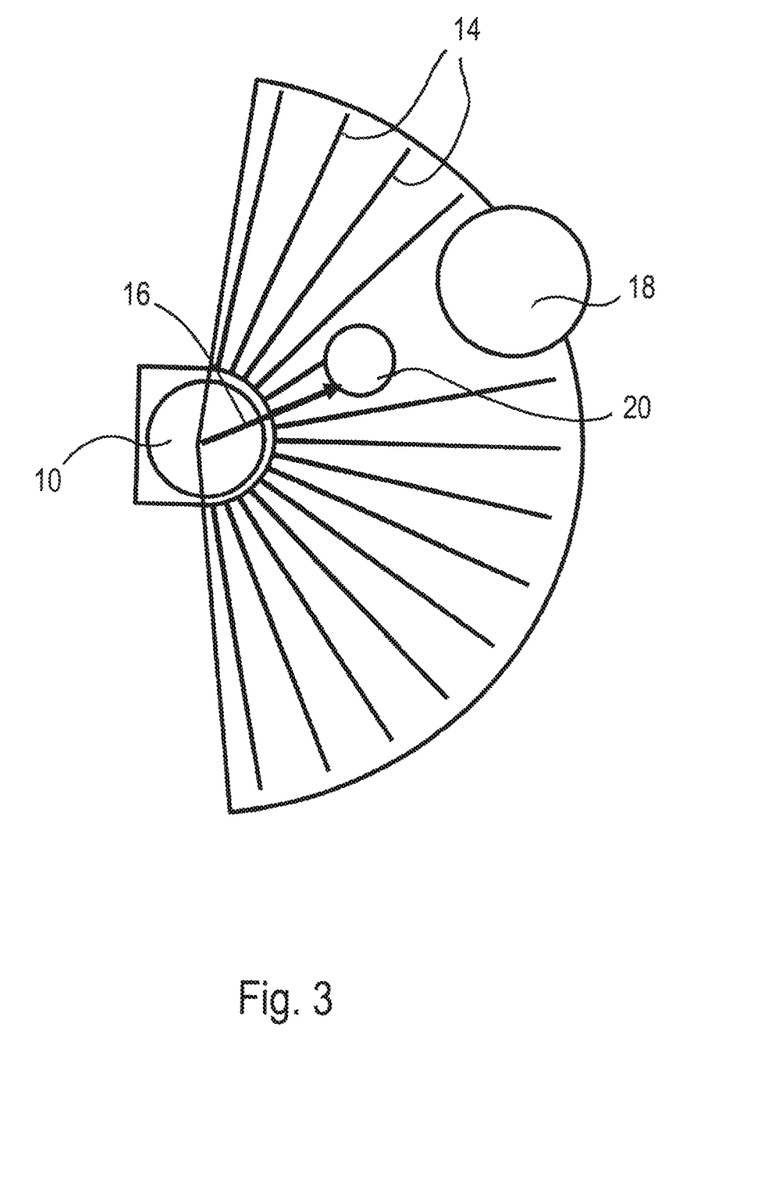

FIGS. 1 to 3 show a distance-measuring monitoring sensor 10, for example a laser scanner, that in the present example monitors a sector-shaped protected field 12 that extends approximately over an angular range of 165°.

The monitoring sensor 10 has a light transmitter for transmitting a transmitted light beam 16 into the protected field 12; a light receiver for receiving light that is reflected or remitted by an object that may be present in the protected field (by a particle 20 or by a large object 18 in the present examples); and a deflection unit that is configured to vary the transmission angle, i.e. the angle at which the transmitted light beam 16 is transmitted with respect to the protected field 12 and, optionally also the received signal, i.e. the angle direction from which the light reflected or remitted with respect to the protected field 12 from an object, synchronously with respect to the transmission angle.

After a specific angle change, a respective light pulse can be transmitted and received light that may be scattered back can be detected. A discrete number of light paths 14 that are scanned consecutively by the monitoring sensor 10 results in this manner. A sector-shaped monitored field is in this respect associated with each light path 14 and extends at both sides of the respective light path 14 since the transmitted light beam 16 does not propagate exactly along one line as shown the present embodiment, but rather has a specific divergence. In the ideal case, the configuration of the monitoring sensor 10 takes place such that the monitored fields associated with the light paths 14 are adjacent to one another. Adjacent monitored fields can, however, also overlap or can be spaced apart from one another to a specific degree. Fifteen light paths 14 or monitored fields are provided in the present example.

In principle, the present invention is not restricted to a laser scanner in which the individual light paths 14 are scanned consecutively in time. All the light paths 14 or groups of light paths 14 can also be synchronously scanned, which requires a corresponding number of light transmitter/receiver pairs. The monitoring sensor 10 furthermore does not necessarily have to have only one single scanning surface that is defined by the plane of the drawing in the present example, but can rather also have a plurality of scanning surfaces, e.g. a plurality of scanning planes spaced apart from one another in parallel or a plurality of conical scanning surfaces having different azimuth angles.

The determination of the spacing from a detected object can take place in a manner known per se on the basis of the time of flight of the transmitted light beam 14 or of the phase shift between the modulated transmitted and received light.

The monitoring sensor 10 can have an integrated control unit that is configured for generating received signals on the basis of the light received from the light receiver. The received signals can specifically comprise information on the angular position of a monitored field and on the distance of the object from the monitoring sensor for this respective monitored field in which light is scattered back from an object.

The protected field 12 is cyclically scanned such that a time sequence of received signals is present for each light path 14 or for each monitored field.

The monitoring sensor 10 can comprise a storage device that stores the received signals on one or more scanning cycles.

The size of a detected object can be determined on the basis of the determined distance of the object from the monitoring sensor 10 and on the basis of the determined size of the angular range over which the detected object extends. The determination of the size of the angular range over which the object extends can in particular be determined on the basis of the number of adjacent monitored fields that are infringed by the presence of the object and on the basis of their angle intervals.

A possible method for a classification whether a detected object is to be classified as a large object 18 or as a particle 20 will be explained with respect to the table in FIG. 4. This table relates to an exemplary embodiment of a monitoring sensor that does not have to coincide with the monitoring sensor 10 of FIGS. 1 to 3. There can in particular be differences with respect to the number of monitored fields and their angle intervals.

Figure 4:
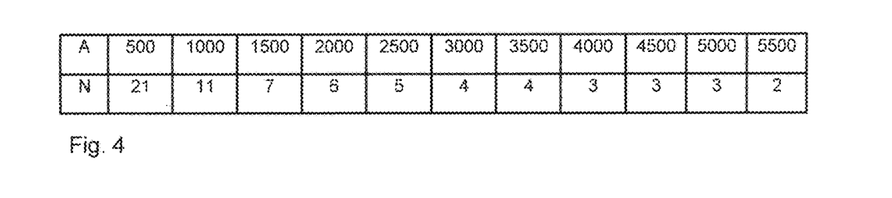
FIG. 4 a table in which the minimum number of infringed monitored fields required for a classification of an object as a large object is indicated in dependence on the distance by way of example.

Different distances A are indicated in millimeters in the upper line of the table in accordance with FIG. 4. A number N of monitored fields is associated with each distance A and has to be infringed by at least one object at the respective distance so that an object is classified as a large object. If this number of infringed monitored fields is not reached, the respective object is classified as a particle.

In the constellation shown in FIG. 1, there is a large object 18 at a distance r within the protected field 12. Two adjacent monitored fields are infringed in this constellation due to the size of the large object 18 and its distance from the monitoring sensor 10. The classification as a large object 18 takes place here on the basis of a predefined threshold value for the size of an object at which the monitoring sensor 10 should output an object detection signal because there is, for example, the risk that the detected object could be a human limb. A size of 70 mm can be predefined as the threshold value, for example.

In the constellation of FIG. 2, the large object 18 is now at a distance r/2 from the monitoring sensor 10. A total of four adjacent monitored fields are infringed in this constellation due to the smaller distance.

In the constellation of FIG. 3, the large object 18 is again at the distance r from the monitoring sensor 10 (corresponding to FIG. 1).

There is still a smaller object in the protected field 12 whose size is smaller than the predefined threshold value and that is therefore classified as a particle 20. A classification as a particle 20 takes place, for example, for such objects from which no risk to a user can be assumed, for example chips, snowflakes, raindrops or dust particles that fly around.

As can easily be recognized in FIG. 3, the particle 20 in the present constellation infringes the same monitored fields as the large object 18. The particle 20 so-to-say casts a shadow over the large object 18. With a monitoring sensor that would focus only on the size of the detected object in the generation of an object detection signal, no object detection signal would be generated in the constellation shown in FIG. 3 since only the particle 20 is detected and it is considered as non-critical to safety due to its classification. The protected field infringement critical to safety due to the large object 18 cannot be detected due to the shadowing. The constellation shown in FIG. 3 therefore represents a safety-critical situation.

To be able to carry out a better differentiation between safety-critical and non-safety critical objects, the time development of the positions of objects is also taken into account in addition to the size of these objects that are located within the protected field 12 within a specific scanning cycle, i.e. not only a single scanning cycle is observed per se, but rather a plurality of sequential scanning cycles. It can be determined on the basis of this time differentiation whether an object is present in the protected field 12 at a stationary angle or movable at least with respect to its angular position.

Accordingly different cases are defined in which the respective criteria for the generation of an object detection signal are present:

In a first case, the presence of an object classified as a large object is detected for a predefined first number of scanning cycles. The object detection signal is generated independently of whether the large object is static or moving.

In a second case, an object detection signal is generated when at least one object classified as a particle was detected in the protected field, with this particle additionally having to satisfy the condition that is has to be at a stationary angle, i.e. has to be substantially located in the same monitored field. Since a particle 20 that is actually at a stationary angle and that only infringes a single monitored field due to its size and position can be present at the border of two adjacent monitored fields, it can be detected, for example, either in the one monitored field or in the other monitored field due to measuring inaccuracies in different scanning cycles.

That case can thus also be considered as at a stationary angle that a particle alternately infringes two monitored fields directly adjacent to one another in different scanning cycles. The case that, for example, a specific monitored field is infringed in one scanning cycle and an further directly adjacent monitored field is infringed in a following cycle can be considered as at a stationary angle.

The fact is utilized in the method in accordance with the invention that particles penetrating into the protected field are classified as non-critical due to their size for as long as they are in motion since it is unlikely that they mask a large object that is safety-critical per se over the total observed period of time. To do this, the particle would have to move at the same speed or angular speed and in the same direction as the large object. Since this will only occur with an extremely small probability, this case can be neglected so that the availability of a machine to be monitored using the monitoring sensor in accordance with the invention can be considerably increased since particles that penetrate into the protected field and that are not safety-critical due to their size do not produce a false-positive generation of an object detection signal.

The possibly critical case that a large object that is safety-critical per se is masked by such a particle and therefore remains undetected is prevented by the criterion according to which a particle at a stationary angle nevertheless triggers an object detection signal. The increase in availability is thus not at the cost of safety.

With the two above-described case constellations, it is necessary for the generation of an object detection signal that a movable large object or a large object at a stationary angle and in particular stationary, and/or a particle at a stationary angle each have to be present in the protected field for a specific period of time or for a predefined number of cycles. A constellation is, however, conceivable in which a large object is only detected at times during an observed number of cycles because it is, for instance, masked by a particle for some of the scanning cycles, with the particle only being present during some of the observed scanning cycles.

Provision can be made for this third case in accordance with an advantageous modification that an object detection signal is also generated as a precaution when at least one large object and at least one particle are respectively located in at least one of the monitored fields for at least some of these cycles, wherein they do not necessarily always have to be present in the same monitored field or fields for the duration of their detection in these sequential cycles. In other words, in such a scenario, any desired combination of particles and large objects that are present in the protected field during a predefined number of sequential scanning cycles can result in a generation of an object detection signal. Safety can be further increased by using this additional criterion, with a certain impairment of availability being possible, however, Exemplary methods with which the distinctions required for the generation of the object detection signals can be made will be described in the following with reference to the tables in FIGS. 5 to 7.

On the one hand, a large object index is defined that is incremented by 1 starting at 0 when the presence of at least one large object is determined independently of its position within a respective scanning cycle. If it is found in one of the following cycles that there is no large object within the protected field, the large object index is reset to 0. The number of sequential scanning cycles in which at least one large object is present in the protected field is thus counted by means of the large object index. If the large object index has reached a predefined number of scanning cycles, an object detection signal is generated.

On the other hand, an associated particle index is defined for each monitored field that is respectively incremented by 1 starting at 0 when the presence of a particle was determined in this monitored field. If a particle previously present in a specific monitored field is no longer detected in this monitored field in a subsequent scanning cycle, the respective particle index is reset to 0 again.

In order also to be able to detect those particles that are only substantially at a stationary angle in the initially explained sense because they e.g. appear to "jump" between two adjacent monitored fields, not only the particle index associated with the directly infringed monitored field can be incremented in accordance with a modification, but also the respective particle index of one or more monitored fields adjacent thereto. A resetting of these particle indices to 0 can in particular take place when a particle was no longer detected in any of these monitored fields in a subsequent scanning cycle.

The maximum of the particle indices is determined for each scanning cycle for the generation of an object detection signal. When the maximum of all particle indices has reached a predefined number, an object detection signal is generated. Since moving particles typically have the result that the particle index of a respective monitored field is reset to 0 again because the particle has already left this monitored field again after a small number of scanning cycles and the named maximum thus does not reach the predefined number, the criterion for the triggering of an object detection signal is not satisfied for these moving particles. Only when a particle at a stationary angle is always present in the same monitored field (or in a monitored field directly adjacent thereto) over a number of scanning cycles corresponding to the named predefined number will the maximum reach the predefined number and result in the triggering of an object detection signal.

Provision can be made in order also to take account of the detection criterion in accordance with the named third case that a total index is formed as the sum of the large object index and the maximum of the particle indices, with an object detection signal being generated when the total index has reached a predefined number.

The above-described methods will be described in the following with respect to the tables in FIGS. 5 to 7 for different exemplary object constellations, with a number of further object constellations naturally being conceivable in addition to the described object constellations and with the list thus not being exclusive.

Figure 5:
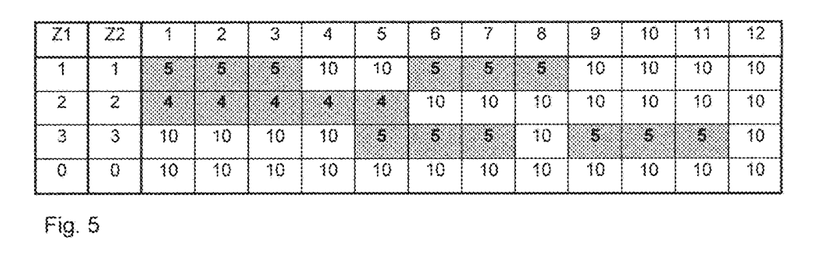
FIGS. 5 to 7 tables that reproduce received signals for different object constellations in the protected field of a monitoring sensor in a schematic manner.
Figure 6:
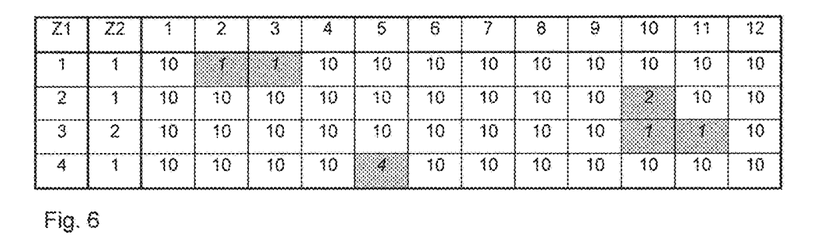
Figure 7:
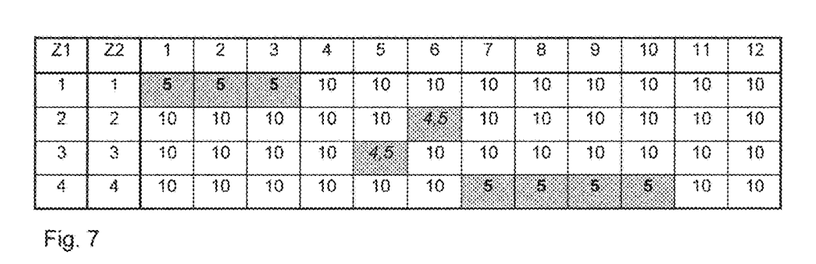

In the tables of FIGS. 5 to 7, two different indices Z1, Z2 are indicated in the first two columns whose meaning will be explained in more detail in the following. As will result from the corresponding explanation, the indices Z1 or Z2 are not the already described large object index or the already described particle index. The following twelve columns represent respective monitored fields, with the digits in the first line representing respective position numbers of the monitored fields. The second to fifth lines of the table each stand for four sequential scanning cycles of the monitoring sensor. Respective measured distance values for a respectively detected object are given in meters in the table boxes defined by the positions numbers 1 to 12 and the lines 2 to 5. A value of 10 here stands for a monitored field that is free of objects. Monitored fields for which an object was detected are shaded in gray, with the respective distance value being printed in bold when they represent a large object and being printed in italics when they represent a particle.

The index value Z2 represents the named total index that is composed as mentioned of the large object index and the sum of all the particle indices. To illustrate the difference from a conventional monitoring sensor that detects all the objects independently of their size and/or movement, a corresponding comparison index Z1 is respectively indicated in the first column of the tables and is incremented on every detection of an object and is only reset when neither a large object nor a particle was detected in a cycle.

It is assumed with all object constellations in this example that an object detection signal is generated when the total index Z2 or the comparison index Z1 has reached the value 4.

FIG. 5 represents an object constellation in which two large objects that are not at a stationary angle are located within the protected field during three sequential scanning cycles. In the first three scanning cycles, the large object index is respectively incremented by 1 so that it amounts to 3 after the third scanning cycle. Since the large objects are no longer located within the protected field in the fourth scanning cycle, the large object index is reset to 0. Since no particles were detected in the object constellation of FIG. 5, the total index Z2 corresponds to the large object index.

The comparison index Z1 behaves in accordance with the total index Z2.

In the object constellation underlying the table of FIG. 6, a plurality of particles move randomly through the protected field. Particles are located in the monitored fields 2 and 3 in the first scanning cycle. The particle indices of these monitored fields are accordingly incremented by 1 starting at 0. The maximum of the particle indices and thus the total index Z2 amounts to 1. In the second scanning cycle, the particle indices of the monitored fields 2 and 3 are reset and in turn the particle index of the monitored field 10 is incremented to 1. The maximum of the particle indices, and based on this the total index Z2, thereby remains at the value 1. In the third scanning cycle, the particle approaches the monitoring sensor a little and is detected a second time in the monitored field 10 and additionally also for the first time in the monitored field 11. The particle index of the monitored field 10 incremented to 2 has the result that the maximum and thus also the total index Z2 reaches the value 2. In the fourth scanning cycle, the monitored fields 10 and 11 are free again so that the corresponding particle indices are reset. Since, however, a particle is detected for the first time in the monitored field 5, this has the result that the maximum and thus the total index Z2 adopt the value 1. An object detection signal is, however, not triggered in accordance with the method in accordance with the invention since the total index Z2 does not reach the limit value 4.

Unlike this, in a conventional monitoring sensor, each detection of a particle results in an incrementing of the comparison index Z1 so that an object detection signal is generated after the fourth scanning cycle, which is, however, to be evaluated as a false-positive result. An advantage of the method in accordance with the invention is thus revealed here since it avoids such false-positive object detection signals and thus increases the availability of a connected machine.

Finally, the table in accordance with FIG. 7 represents an object constellation in which an object is first detected, disappears behind a particle for two cycles and is detected again in a fourth cycle. In the first scanning cycle, a large object is detected and has the result that the large object index and thus the total index Z2 adopts the value 1. In the second scanning cycle, the large object disappears, with a particle, however, being detected at a different position instead. A resetting of the large object index is omitted due to this directly following detection of a particle. In addition, the particle index for the monitored field 6 is set to 1 so that the total index Z2 adopts the value 1+1=2. In the third scanning cycle, a particle is in turn detected that is detected in the monitored field 5 while the monitored field 6 is recognized as free. Since the monitored fields 5 and 6 are directly adjacent and since the distance values are also identical (4.5 m), it is assumed that it is a particle at a stationary angle. The particle index of the monitored field 6 is thus incremented by 1 to 2 in the third scanning cycle. The total index value Z2 thus adopts the value 3 that is composed of a large object index value 1 and a maximum value 2 of the particle indices. In the fourth scanning cycle, the particle no longer appears in the monitored field 5 or 6; however, in turn a large object is detected in monitored fields 7 to 10. Since in turn no free protected field was recognized, a resetting of the particle indices of the monitored fields 5 and 6 is omitted and the large object index is incremented by 1 to 2. The total index value Z2 thus adopts the value 4 that is composed of a large object index value 2 and a maximum of the particle indices of 2.

A comparison of the method in accordance with the invention with the conventional method for the object constellation in accordance with FIG. 7 with reference to the index values Z1 and Z2 shows that an object detection signal is generated in both cases and thus the object constellation that forms the basis of FIG. 7 is reliably recognized by the method in accordance with the invention and results in a shutdown of a connected machine.

In the described examples, a light path respectively corresponds to an individual monitored field. It is, however, generally also possible that two or more respective light paths are combined to form one monitored field.

REFERENCE NUMERAL LIST

10 monitoring sensor
12 protected field
14 light path
16 transmitted light beam
18 large object
20 particle

The invention claimed is:
1. A method of operating a distance-measuring monitoring sensor for monitoring an at least two-dimensional protected field that is divided into a plurality of sector-shaped, cyclically scannable monitored fields, wherein the monitor- ing sensor comprises at least one light transmitter and at least one light receiver, comprising the steps:

transmitting a transmitted light beam into the protected field by the at least one light transmitter;

receiving light by the at least one light receiver, with the light being reflected or remitted by an object if the object is present in the protected field;

generating a specific received signal for the respective monitored field on the basis of the received light, wherein a respective received signal comprises information on the angular position of the monitored field and on the distance of an object located therein from the monitoring sensor, wherein all of the plurality of the monitored fields of the protected field are scanned once within a cycle;

determining the size of an angular region over which a respective detected object extends;

determining the size of the object on the basis of the determined distance and on the basis of the determined size of the angular region;

classifying the object as a particle or as a large object on the basis of the determined size of the object and of a predetermined threshold value for the size, wherein the object is classified as a particle if it is smaller than the threshold value and is classified as a large object if it is larger than the threshold value; and generating an object detection signal on the basis of the received signals when it is found that at least one large object is located in at least one of the monitored fields for a predefined first number of sequential cycles or when it is found that at least one particle is located substantially at a stationary angle in at least one of the plurality of monitored fields for a predefined second number of sequential cycles.

2. The method in accordance with claim 1, wherein the first number and the second number are the same.

3. The method in accordance with claim 1, wherein an object detection signal is furthermore also generated when it is found for a predefined third number of sequential cycles that at least one large object and at least one particle are each located in at least one of the plurality of monitored fields for at least some of these cycles.

4. The method in accordance with claim 1, wherein an object detection signal is furthermore also generated when it is found for a predefined third number of sequential cycles that at least one large object and at least one particle are each located in at least one of the plurality of monitored fields for at least some of these cycles and the at least one particle is substantially at a stationary angle.

5. The method in accordance with claim 1, wherein a large object index is provided and a respective particle index is provided for each monitored field;

wherein the determination whether at least one large object is located in at least one of the plurality of monitored fields for a predefined first number of sequential cycles comprises the large object index being incremented by 1 when the presence of at least one large object was detected in one cycle and the generation of the object detection signal comprises an object detection signal being generated when the large object index reaches the predefined first number; and wherein the determination whether at least one particle is located in at least one monitored field substantially at a stationary angle for a predefined second number of sequential cycles comprises a respective particle index being incremented by 1 in a respective cycle when the presence of a particle in the monitored field associated with this particle index or in a directly adjacent monitored field was detected in a cycle and the generation of the object detection signal comprises the maximum of all particle indices being determined and an object detection signal being generated when the maximum has reached the predefined second number.

6. The method in accordance with claim 5, wherein an object detection signal is furthermore also generated when it is found for a predefined third number of sequential cycles that at least one large object and at least one particle are each located in at least one of the plurality of monitored fields for at least some of these cycles, wherein the generation of an object detection signal comprises, when it is found for a predefined third number of sequential cycles that at least one large object and at least one particle are respectively located in at least one of the plurality of monitored fields for at least some of these cycles, the sum of the large object index and the maximum of the particle indices being formed and the object detection signal being generated when the sum has reached the predefined third number.

7. The method in accordance with claim 6, wherein the determination whether at least one large object is located in at least one of the plurality of monitored fields for a predefined first number of sequential cycles furthermore comprises the large object index being reset when the absence of large objects was detected in a cycle; wherein a resetting of the large object index is omitted when the presence of a particle was detected at the same time within that cycle in which the absence of a large object was detected that was present in the preceding cycle.

8. The method in accordance with claim 6, wherein the finding whether at least one particle is present in at least one of the plurality of monitored fields substantially at a stationary angle for a predefined second number of sequential cycles furthermore comprises a respective particle index being reset in a respective cycle when the presence of a particle was detected for the associated detection field in the directly preceding cycle and the absence of this particle was detected in the current cycle;

wherein a resetting of the large object index is omitted when the presence of a particle was detected at the same time within that cycle in which the absence of a large object was detected that was present in the preceding cycle.

9. The method in accordance with claim 6, wherein the determination whether at least one large object is located in at least one of the plurality of monitored fields for a predefined first number of sequential cycles furthermore comprises the large object index being reset when the absence of large objects was detected in a cycle; wherein a resetting of the particle index is omitted when the presence of a large object was detected at the same time within that cycle in which the absence of a particle was detected that was present in the preceding cycle.

10. The method in accordance with claim 6, wherein the finding whether at least one particle is present in at least one of the plurality of monitored fields substantially at a stationary angle for a predefined second number of sequential cycles furthermore comprises a respective particle index being reset in a respective cycle when the presence of a particle was detected for the associated detection field in the directly preceding cycle and the absence of this particle was detected in the current cycle;

wherein a resetting of the particle index is omitted when the presence of a large object was detected at the same time within that cycle in which the absence of a particle was detected that was present in the preceding cycle.

11. The method in accordance with claim 5, wherein an object detection signal is furthermore also generated when it is found for a predefined third number of sequential cycles that at least one large object and at least one particle are each located in at least one of the plurality of monitored fields for at least some of these cycles and the at least one particle is substantially at a stationary angle, wherein the generation of an object detection signal comprises, when it is found for a predefined third number of sequential cycles that at least one large object and at least one particle are respectively located in at least one of the plurality of monitored fields for at least some of these cycles, the sum of the large object index and the maximum of the particle indices being formed and the object detection signal being generated when the sum has reached the predefined third number.

12. The method in accordance with claim 11, wherein the determination whether at least one large object is located in at least one of the plurality of monitored fields for a predefined first number of sequential cycles furthermore comprises the large object index being reset when the absence of large objects was detected in a cycle;

wherein a resetting of the large object index is omitted when the presence of a particle was detected at the same time within that cycle in which the absence of a large object was detected that was present in the preceding cycle.

13. The method in accordance with claim 11, wherein the finding whether at least one particle is present in at least one of the plurality of monitored fields substantially at a stationary angle for a predefined second number of sequential cycles furthermore comprises a respective particle index being reset in a respective cycle when the presence of a particle was detected for the associated detection field in the directly preceding cycle and the absence of this particle was detected in the current cycle;

wherein a resetting of the large object index is omitted when the presence of a particle was detected at the same time within that cycle in which the absence of a large object was detected that was present in the preceding cycle.

14. The method in accordance with claim 11, wherein the determination whether at least one large object is located in at least one of the plurality of monitored fields for a predefined first number of sequential cycles furthermore comprises the large object index being reset when the absence of large objects was detected in a cycle;

wherein a resetting of the particle index is omitted when the presence of a large object was detected at the same time within that cycle in which the absence of a particle was detected that was present in the preceding cycle.

15. The method in accordance with claim 11, wherein the finding whether at least one particle is present in at least one of the plurality of monitored fields substantially at a stationary angle for a predefined second number of sequential cycles furthermore comprises a respective particle index being reset in a respective cycle when the presence of a particle was detected for the associated detection field in the directly preceding cycle and the absence of this particle was detected in the current cycle;

wherein a resetting of the particle index is omitted when the presence of a large object was detected at the same time within that cycle in which the absence of a particle was detected that was present in the preceding cycle.

16. The method in accordance with claim 5, wherein the determination whether at least one large object is located in at least one of the plurality of monitored fields for a predefined first number of sequential cycles furthermore comprises the large object index being reset when the absence of large objects was detected in a cycle.

17. The method in accordance with claim 5, wherein the finding whether at least one particle is present in at least one of the plurality of monitored fields substantially at a stationary angle for a predefined second number of sequential cycles furthermore comprises a respective particle index being reset in a respective cycle when the presence of a particle was detected for the associated detection field in the directly preceding cycle and the absence of this particle was detected in the current cycle.

18. The method in accordance with claim 1, wherein the determination of the size of an angular region over which a respective object extends comprises the size of the angular region being determined on the basis of the number of adjacent monitored fields in which the presence of an object was found at substantially the same distance and their angular intervals being determined.

19. The method in accordance with claim 1, wherein the received signals generated during a respective cycle are stored for a predefined number of cycles and the object detection signal is generated on the basis of the stored received signal.

20. The method in accordance with claim 1, wherein the monitoring sensor is a laser scanner that is configured for monitoring one or more scanning surfaces.

21. A distance-measuring monitoring sensor for monitoring an at least two-dimensional protected field that is divided into a plurality of sector-shaped, cyclically scannable monitored fields, wherein the monitoring sensor comprises at least one light transmitter, at least one light receiver and a control unit, with the control unit being configured for carrying out the method in accordance with claim 1.

* * * * *